United States Patent
Chu et al.

(10) Patent No.: US 11,747,248 B2
(45) Date of Patent: Sep. 5, 2023

(54) METHOD FOR ASSESSING THE VOLATILE RELEASE PERFORMANCE OF MICROCAPSULES

(71) Applicant: GIVAUDAN SA, Vernier (CH)

(72) Inventors: Shih-Chi Chu, Ashford (GB); Angus Peter Macmaster, Romney Marsh (GB); Marcus James Goodall, Canterbury (GB)

(73) Assignee: Givaudan SA, Vernier (CH)

( * ) Notice: Subject to any disclaimer, the term of this patent is extended or adjusted under 35 U.S.C. 154(b) by 207 days.

(21) Appl. No.: 17/044,988

(22) PCT Filed: Apr. 16, 2019

(86) PCT No.: PCT/EP2019/059806
§ 371 (c)(1),
(2) Date: Oct. 2, 2020

(87) PCT Pub. No.: WO2019/201920
PCT Pub. Date: Oct. 24, 2019

(65) Prior Publication Data
US 2021/0164873 A1    Jun. 3, 2021

(30) Foreign Application Priority Data
Apr. 17, 2018   (GB) ..................... 1806240

(51) Int. Cl.
*G01N 3/24* (2006.01)
*C11D 3/50* (2006.01)
*G01N 33/00* (2006.01)

(52) U.S. Cl.
CPC ............ *G01N 3/24* (2013.01); *C11D 3/505* (2013.01); *G01N 33/0036* (2013.01); *G01N 2203/0025* (2013.01); *G01N 2203/0032* (2013.01)

(58) Field of Classification Search
CPC ............ G01N 3/24; G01N 2203/0032; G01N 2203/0025; G01N 33/0036; C11D 3/505
See application file for complete search history.

(56) References Cited

U.S. PATENT DOCUMENTS

2016/0083537 A1* 3/2016 Shimba ................... H01L 24/83
264/299

FOREIGN PATENT DOCUMENTS

| WO | 2016207179 A1 | 12/2016 | | |
| WO | WO-2016207179 A1 * | 12/2016 | ............... | A61K 8/11 |

OTHER PUBLICATIONS

International Search Report and Written Opinion of the International Searching Authority for corresponding application PCT/EP2019/059806 dated Jul. 19, 2019.
(Continued)

*Primary Examiner* — Jamel E Williams
(74) *Attorney, Agent, or Firm* — Norris McLaughlin PA

(57) ABSTRACT

A method for assessing the release performance of microcapsules comprising at least one volatile ingredient, the method comprising the steps of:
a. applying a plurality of said microcapsules to an underlying surface;
b. applying a kinetic frictional shear stress τ through a contact surface of a probe under a predefined load, a predefined contact surface area and a predefined shear rate to said plurality of microcapsules; and
c. measuring the amount of the at least one volatile ingredient released per second from said microcapsules under said kinetic frictional shear stress τ.

13 Claims, 2 Drawing Sheets

(56) References Cited

OTHER PUBLICATIONS

GB Search Report for corresponding application GB 1806240.6 dated Oct. 12, 2018.
J. Bartsch, et al: "Analysis of odour compounds from scented consumer products using gas chromatography-mass spectrometry and gas chromatography-olfactometry"; Analytica Chimica Acta (Elsevier, NL); vol. 904; Nov. 27, 2015; p. 98-106; XP029372883.
E. Ansarifar, et al: Novel multilayer microcapsules based on soy protein isolate fibrils and high methoxyl pectin: Production, characterization and release modeling; Int. Journal of Biological Macromolecules (Elsevier NL); vol. 97; Jan. 16, 2017; p. 761-769; XP029917969.
S. N. Rodrigues, et al: "Scenfashion® : Microencapsulated perfumes for textile application"; Chem. Engineering Journal (Elsevier, NL); vol. 149; No. 1-3; Jul. 1, 2009; p. 463-471.
J. D. Berry: "Precise measurements of capsule mechanical properties using indentation"; Soft Matter, 2017, 13, 1943.

\* cited by examiner

METHOD FOR ASSESSING THE VOLATILE RELEASE PERFORMANCE OF MICROCAPSULES

This is an application filed under 35 USC 371 based on PCT/EP2019/059806, filed 16.Apr.2019, which in turn is based on GB 1806240.6 filed 17.Apr.2018. The present application claims the full priority benefit of these prior applications and herein incorporates by reference the full disclosures of these prior applications.

FIELD OF THE INVENTION

The present invention relates to a method for assessing the release performance of microcapsules.

BACKGROUND OF THE INVENTION

Microcapsules are widely used to provide controlled release of functional ingredients, such as biocides, catalysts, vitamins, cosmetic actives, flavours and fragrances. The benefit of these microcapsules is that they release the right amount of functional ingredients where and when this functional ingredient is needed. This is particularly important for volatile ingredients, where evaporation is advantageously reduced or even completely suppressed by encapsulation. On the other hand, volatile ingredients are easily released by solubilizing, heating, breaking and/or squeezing the microcapsules. Hence, microcapsules have been widely used to control and improve the performance of flavours and fragrances, which contain a substantial amount of volatile ingredients.

The way microcapsules respond to mechanical forces is an important parameter determining the release performance.

WO 2010/084480 A2 discloses a method for determining the fracture strength of core-shell microcapsules having an amino (meth)acrylate shell: First, the rupture force of 50 individual particles is determined using the procedure given in Z. Zhang; G. Sun; "Mechanical Properties of Melamine-Formaldehyde microcapsules," J. Microencapsulation 18 (2001) 593-602. Then, the fracture strength of each particle is calculated by dividing the rupture force (in Newton) by the cross-sectional area of the respective spherical particle ($\pi r^2$, where r is the radius of the particle before compression).

However, this so-called "indentation method" has a number of drawbacks that make it not ideal for predicting the effective mechanical behaviour of core-shell microcapsules in an application. In particular, as documented in the examples hereinafter, the fracture strength values provided by applying the indentation method on encapsulated fragrance compositions hardly correlate with the olfactive performance scores observed by panellists.

One problem of the indentation method is that it is based on measuring the force at rupture under indentation conditions, wherein the direction of indentation is perpendicular to a hard substrate surface supporting the microcapsule, such that the sum of all shear components of the stress is zero. This situation is unlikely to occur under real life conditions, where deformation forces are usually not perpendicular to the substrate surface and, therefore, at least one shear component of the stress is not zero.

A second problem of the indentation method is that the rupture force is measured on a hard substrate surface. This means that when applying a normal force, all the energy is dissipated in deforming only the microcapsule. Real substrates of interest for microcapsule applications, such as fabrics, hair, skin, etc. are deformable. This means that, for a given deformation force, the effective deformation of the capsule is smaller than the nominal value that would be obtained on a rigid substrate. As a consequence, the fracture strength of the microcapsule is significantly under-estimated if the effect of substrate deformation is not taken into account. The under-estimation may be up to 100%, as reported by J. D. Berry, S. Mettuab and R. R. Dagastine, Soft Matter, 13 (2017) 1943-1947.

Further disadvantages of the indentation method are the duration of the measurements.

There is therefore a need for a new microcapsule assessment method that is more in line with the situation in real life applications. There is also a need for improved microcapsules having an optimal release profile under real conditions.

SUMMARY OF THE INVENTION

The applicant has surprisingly found that microcapsules submitted to a kinetic frictional shear stress under a predefined load, a predefined contact surface area and a predefined shear rate, are deformed and/or fractured in such a way that the amount of volatile ingredients released from the microcapsules correlates in a most satisfactory manner to the microcapsule olfactive performance score assessed by panelists under real life conditions.

Hence, in a first aspect, there is provided a method for assessing the release performance of microcapsules comprising at least one volatile ingredient, the method comprising the steps of:

a) applying a plurality of said microcapsules to an underlying surface;

b) applying a kinetic frictional shear stress through a contact surface of a probe under a predefined load p, a predefined contact surface area and a predefined shear rate to said plurality of microcapsules; wherein:

the contact surface area is defined as the area of the contact surface of the probe through which the predefined load is applied; and the shear rate is defined as the velocity u of said probe relative to the underlying surface in a direction parallel to said underlying surface divided by the distance between the probe and the underlying surface;

and c) measuring the amount of the at least one volatile ingredient released per second from said microcapsules under said kinetic frictional shear stress $\tau$.

By "volatile ingredient" is meant an ingredient having an equilibrium vapour pressure of more than 0.001 Pa at 20° C.

Kinetic frictional shear stresses may be applied to microcapsules by many different ways. For example, a kinetic frictional shear stress may be produced by rubbing a layer of neat microcapsules deposited on a hard surface or rubbing or squeezing a deformable material comprising microcapsules. Alternatively, the microcapsules may be embedded in a deformable material and this deformable material submitted to an elongational traction. In such methods, however, the kinetic frictional shear stress applied to the microcapsules is not well defined. One particularly suitable way to apply a well-defined kinetic frictional shear stress to microcapsules is to use a tribometer. Tribometers may have different geometries, such as a pin-on-disc or pin-on-plate geometry. In a pin-on-plate tribometer, the kinetic frictional shear stress is applied by moving a pin probe back and forth on the material to be tested, whereas in a pin-on-disc tribometer, an immobile pin probe is applied to a rotating disc supporting the material to be tested.

So-called powder rheometers consisting of two parallel, counter-rotating plate-plate, cone-plate or cylinder-dash pot arrangements may also be used. Any rheometer allowing the application of a load on a sample under shear deformation may also be used, wherein the load is applied perpendicularly to the shear plane.

All of these systems can provide a suitable combination of load and displacement for producing the desired stresses. However, rheometers are not easily adapted for testing samples containing volatile ingredients that may emanate from the cell where the kinetic frictional shear stress is applied.

One preferred way to apply a well-defined kinetic frictional shear stress to microcapsules is to use a pin-on-plate tribometer, as discussed below.

The application of a sufficient kinetic frictional shear stress to the microcapsules induces the release of at least part of the at least one volatile ingredient; and the amount released may be determined by using analytical methods known to the art.

In an embodiment, the microcapsules are core-shell microcapsules or particles in which the at least one volatile ingredient is distributed in the form of a plurality of inclusions and/or droplets. The latter form is also referred to as "matrix microcapsules". Core-shell microcapsules are well-known in the fragrance and flavour industry, and include for instance core-shell microcapsules obtained by gelatine coacervation or gelatine complex coacervation with carboxymethyl cellulose or acacia gum, and core-shell microcapsules having a shell comprising a thermosetting resin, such as an aminoplast resin, a polyurea resin or a polyacrylate resin. An example of a matrix microcapsule is a spray-dried particle obtained by spray-drying a flavour oil-in-water emulsion comprising hydrophilic encapsulation materials, such as carbohydrates, for instance. Beads obtained by dripping a flavour oil-in-water emulsion comprising alginate into a calcium chloride solution comprise a plurality of oil droplets distributed throughout a hydrogel and correspond also to the definition of matrix microcapsules. These systems are well-known to the skilled person.

In an embodiment, the at least one volatile ingredient is a flavour or a fragrance ingredient. It is also possible to combine both flavour and fragrance ingredients.

In an embodiment, the microcapsules are embedded in and/or deposited on a supporting material. Said supporting material is preferably deformable. Suitable supporting materials include, but are not limited to, an adhesive, a granulated material, a powder, a woven material, a non-woven material, a gel, an emulsion, a cream, a polymer, or a combination thereof.

In an embodiment, said supporting material comprises a liquid, such as water, ethanol, glycol, glycol ether or hydrocarbon, a water-in-oil emulsion or an oil-in-water emulsion, such as a cream. The supporting material may be impregnated with the liquid or comprise the liquid in its pores or voids. The supporting material may also be a gel where the liquid coexists with a polymer network, wherein the liquid prevents the network from collapsing and wherein the network prevents the liquid from flowing apart. Such a gel may be a permanent or a transient network.

In an embodiment, the kinetic frictional shear stress is applied by means of a tribometer, preferably a pin-on-plate tribometer.

In a second aspect of the invention, there is provided the use of a tribometer to assess the release performance of microcapsules comprising at least one volatile ingredient.

In a third aspect of the invention, there is provided a composition comprising a plurality of microcapsules in a suspending medium, wherein said microcapsules comprise at least one volatile ingredient and wherein the maximal amount of said at least one volatile ingredient released when upon application of a kinetic frictional shear stress $\tau$ of from $0.5 \times 10^4$ N/m$^2$ to $1 \times 10^4$ N/m$^2$ under a load of 2 N, through a contact surface area of from $5.2 \times 10^{-5}$ m$^2$ to $6 \times 10^{-5}$ m and with a shear rate of $11 \pm 0.25$ s$^{-1}$ is higher than 5 wt % of the maximal amount of releasable volatile ingredient from neat microcapsules deposited on a hard surface upon application of load of 20 N, through a contact surface area of 2.8 mm$^2$ and with velocity of 10/s.

BRIEF DESCRIPTION OF THE DRAWINGS

The present invention is further exemplified by means of the following non-limiting drawings.

Said pin-on-plate tribometer comprises a glass plate A or any other solid substrate; a supporting material B, in which the microcapsules are embedded and/or on which they are deposited, the supporting material B having a thickness h; and a pin probe C with an essentially rectangular surface area s that typically corresponds to the contact surface area in contact with the supporting material B.

The surface of the pin probe in contact with the supporting material may be flat or convex. A convex geometry prevents the supporting material from being torn up when the pin probe is moved back and forth during the measurement, as described hereunder.

Figure 1:
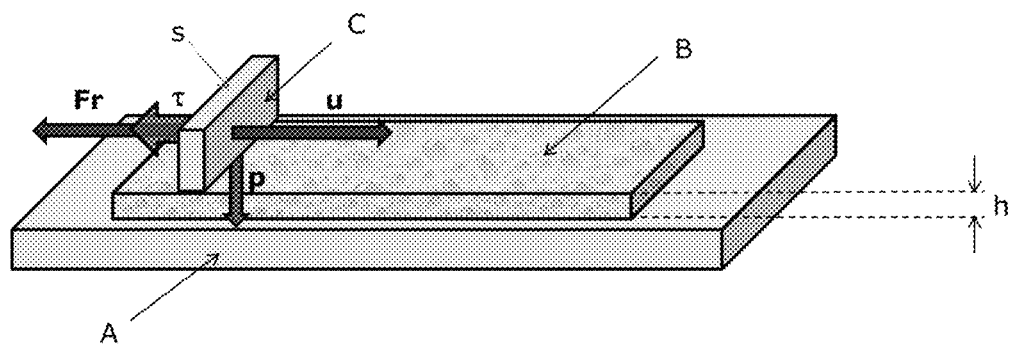
FIG. 1 schematically shows the relevant components of a pin-on-plate tribometer, which is a particularly suitable instrument for executing the method of the present invention.

The geometry shown in FIG. 1 is only representative and schematized. For instance, the pin probe may have different geometries.

Figure 2:
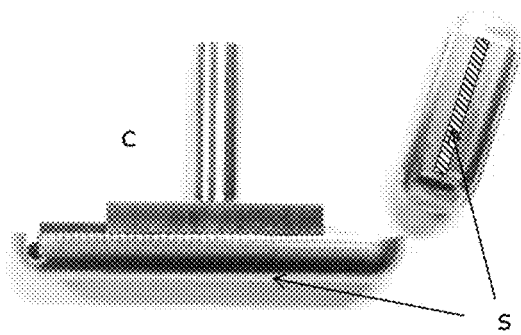

A very suitable geometry is that of a truncated cylinder as shown in FIG. 2. In use, the convex outer surface of the truncated cylinder is in contact with the supporting material. A holder pin is attached to the center of the concave inner surface of the truncated cylinder for fixing the truncated cylinder to the transducer of the tribometer (not shown in FIG. 1). The transducer is transfers the selected load on the pin probe, moves the pin probe and measures the friction force applied to the supporting material, as described in more detail hereunder. In use, the truncated cylinder is moved in such a way that its motion is perpendicular to the principal axis of the truncated cylinder.

Typically, the pin probe is made of a hard material, such as a metal or a ceramic material. The underlying plate and supporting material may have any dimension and shape. However, typically, both the plate and the supporting material are rectangular in shape. A suitable geometry is that of a rectangular strip with the longest dimension in the direction parallel to the motion of the pin probe. The dimension of the shortest dimension should be at least as large as the lateral dimension of the pin probe with respect to the direction of its motion. The dimensions of the underlying plate should be at least as large as the dimensions of the supporting material.

In use, the pin probe C is moved with a velocity u in a direction parallel to the glass plate A. In the drawing, the arrows indicate the measured kinetic frictional force Fr, the load p, and the kinetic frictional shear stress τ. The kinetic frictional force Fr and the kinetic frictional shear stress τ act in the same direction, which is opposite to the direction of the pin probe motion. The load p is another force that acts in a direction which is perpendicular to the direction of both the frictional force Fr and kinetic frictional shear stress τ.

In FIG. 2, the hatched region s indicates the portion of the cylinder which, in use, is effectively in contact with the supporting material. Typically, the supporting material B is deformable and the pin probe C is convex, so that the contact surface area s may increase with increasing load p or may vary depending on the deformability of the supporting material B.

The geometries shown in FIGS. 1 and 2 are not limitative and a wealth of alternative experimental setups may be envisioned that fulfill the requirements of the present invention.

The microcapsules may be embedded in or deposited on the supporting material B. Alternatively, the microcapsules may also be deposited directly on and/or attached to the glass plate A.

When the microcapsules are embedded in or deposited on the supporting material and the supporting material is in contact with the pin probe, then the microcapsules are also, directly or indirectly, in contact with the pin probe. The kinetic frictional shear stress τ applied to the supporting material is therefore transferred to the microcapsules and may induce the release of encapsulated volatile ingredients.

Figure 3:
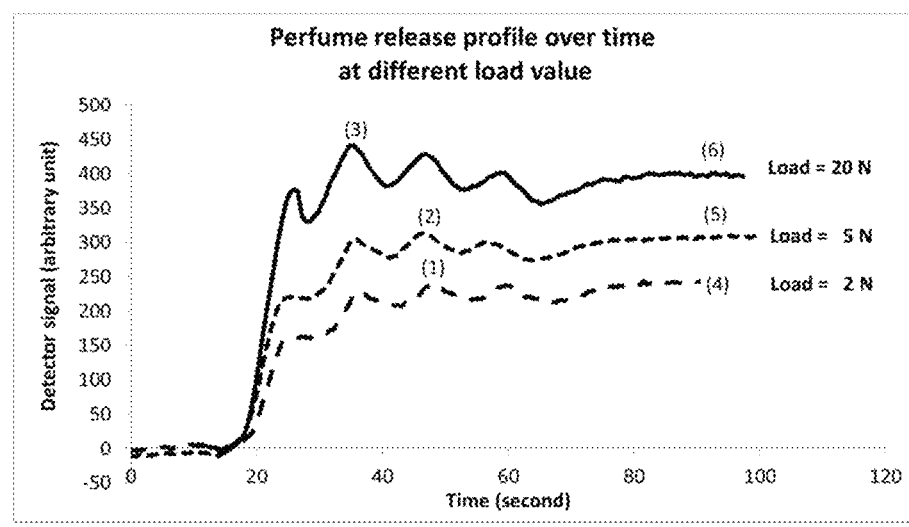

FIG. 3 shows the release curves (4), (5), and (6) of a perfume composition released from aminoplast microcapsules as a function of time and at a load p of 2 N, 5 N, and 20 N, respectively, as measured by a gas detector. The pin probe velocity u was set to 10 mm/s in this case.

The three maxima marked as (1), (2) and (3), respectively, indicate the maximal release value for each of the release curves.

Figure 4:
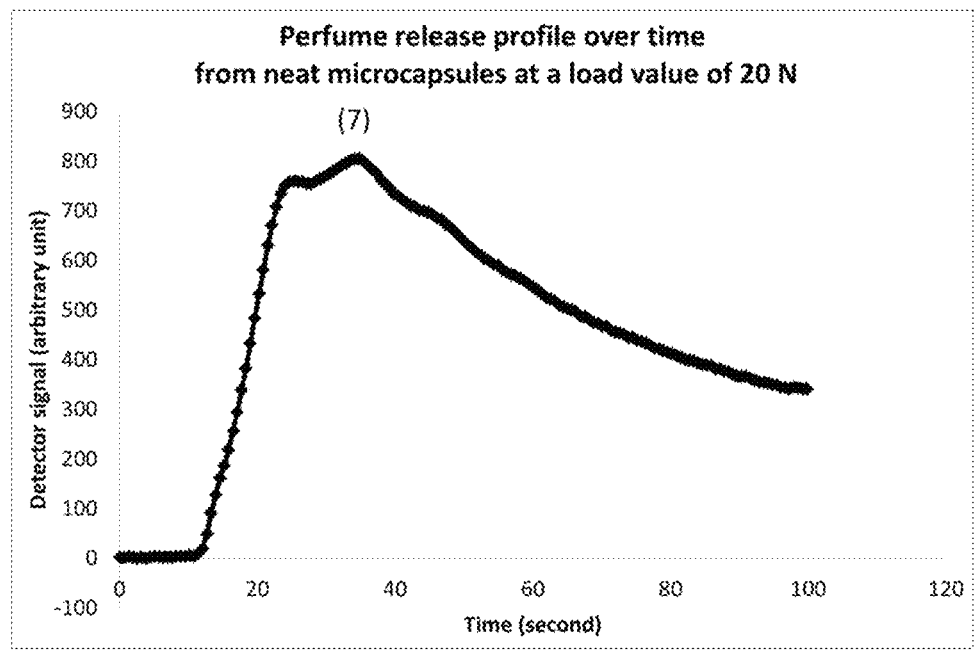

FIG. 4 shows a maximal release curve of neat microcapsules deposited directly on a glass plate, i.e. without a supporting material, and submitted to a load of 20 N, under the same conditions as described hereinabove (except for the supporting material). In this case, however, the contact surface between the pin probe and the hard glass surface is smaller, in order to compensate the lack of deformability of the glass plate. The amount of microcapsules deposited in this case is one tenth of the amount of microcapsules used to measure the release curves (4), (5), and (6) shown in FIG. 3.

The curve in FIG. 4 increases with time, reaches one or more maxima, and then decreases monotonously and is different from those in FIG. 3, which levels up at longer times. This is because in the case of the neat microcapsules, much more microcapsules are broken simultaneously leading to a burst-like perfume release, whereas, with a supporting material, only a smaller portion of the microcapsules are broken each time the pin probe passes on the supporting material, leading to a nearly zero-order perfume release.

The absolute maximum marked as (7) in FIG. 4 is taken as the maximal release value of the neat microcapsules.

DETAILED DESCRIPTION OF THE INVENTION

The applicant discovered that microcapsules submitted to a kinetic frictional shear stress release volatile ingredients according to a profile which is comparable to that encountered in applications of fragrance- or flavor-containing microcapsules in real life. Thus, the method of the present invention allows for mimicking the deformations that such microcapsules effectively experience under day-to-day conditions and offers a convenient alternative to the unpractical and faulty indentation method of the state of the art.

The applicant has therefore developed a method to assess the release performance of perfume-containing microcapsules, and more generally of microcapsules containing at least one volatile ingredient, by applying shear forces to these microcapsules, thereby deforming and/or breaking them. The method of the present invention proved to be a powerful tool for guiding the development of highly performing microcapsules.

The method according to the present invention makes use of the physics of friction (τ, Fr, p and u are written in bold because they are vectorial by nature):

A moving probe in contact with a material through a contact surface area s and exerting a given force (load) p on this material produces a kinetic frictional shear stress τ which is proportional to the applied, measurable friction force Fr divided by the contact surface area s.

If the material is deformable, the kinetic frictional shear stress τ is also proportional to the shear rate, which is given by dividing the probe velocity u by the material thickness h (the position of Fr, u, h, and s are illustrated in FIGS. 1 and 2.)

The friction force itself is proportional to the load p multiplied by the kinetic frictional coefficient $\mu_k$ (dimensionless).

The proportionality constant between the kinetic frictional shear stress τ and the shear rate corresponds to the apparent viscosity η of the supporting material, which is a constant for a given microcapsule bed placed under constant conditions.

The friction force itself is proportional to the load p.

These physical rules are summarized in Equation 1:

$$\tau = Fr/s = \mu_k p/s = \eta(u/h) \quad \text{(Equation 1)}$$

The microcapsules may be disposed directly on an underlying surface, for example a glass surface, or deposited on a supporting material. In this case, the microcapsules are advantageously immobilized. Alternatively or in addition, the microcapsules may be embedded in a supporting material.

The apparent viscosity η of materials may depend on moisture, and therefore, it is preferred that the moisture is controlled and kept constant from one measurement to another. Typically, a relative humidity RH of 45±10% is applied.

A controlled kinetic frictional shear stress τ is applied to the microcapsules by controlling the load p and the shear rate, provided that the kinetic friction coefficient $\mu_k$, as well as the apparent viscosity η and the thickness h of the supporting material, are kept constant. This is achieved by using a well-characterized supporting material, such as a blotting paper or a normed fabric, ensuring constant characteristics from one measurement to another.

Suitable supporting materials that can be used for testing the microcapsules include, but are not limited to, woven or non-woven fabrics, blotting papers, hair swatches, pig skin or model skin, gels, creams and ointments, sponges, foams, powders, and the like. The thickness h of the supporting material is preferably larger than about 0.01 mm, more preferably larger than about 0.1 mm. Preferably, the thickness of the supporting material is smaller than about 1 cm, more preferably smaller than 0.5 cm.

In a particular embodiment, the supporting material is a powder comprising the microcapsules. The powder may be a mineral powder, such as talcum, sodium sulfate and the like, or an organic powder, such as a carbohydrate-based powder.

In a preferred embodiment, the supporting material is a blotting paper or an adsorbing paper sheet having a thickness of from about 0.1 to about 2.5 mm, more particularly from about 0.5 to about 1.5 mm, for example 1±0.1 mm.

In an embodiment, the contact surface area s of the pin probe in contact with the supporting material is from about 1 to about 150 mm$^2$, more particularly from about 10 to about 80 mm$^2$, for example 55±10 mm$^2$.

In an embodiment, the load p applied to the pin probe is from about 0.1 to about 50 N, more particularly from about 0.5 to about 25 N, still more particularly from about 1 to about 10 N, for example 2 N.

When the load p is applied through the pin probe, the supporting material may be deformed, so that the effective thickness for the calculation of the shear rate may have to be corrected. For example, for blotting paper with a thickness of 1 mm, the penetration of the pin probe in the material is typically about 0.08 mm, meaning about 8% referred to the nominal thickness.

In an embodiment, the pin probe velocity u is from about 0.1 to about 100 mm/s, more particularly from about 1 to about 50 mm/s, still more particularly from about 5 to about 25 mm/s, for example 10 mm/s.

The above values correspond to a shear rate of from about 0.04 to about 1000 s$^{-1}$, more particularly from about 1 to about 100 s$^{-1}$, still more particularly from about 4 to about 30 s$^{-1}$, for example 10±2 s$^{-1}$.

In an embodiment, the pin probe is moved back and forth in a direction parallel to the underlying surface, e.g. horizontally, and the load p is applied in a perpendicular direction, e.g. vertically. FIG. 1 illustrates such an arrangement.

Upon application of the kinetic frictional shear stress τ to the microcapsules, the latter may deform or even break. Both deformation and breakage may induce the release of the at least one volatile ingredient from the microcapsules. The ease of deformation and/or breakage is a function of (i) the microcapsule size, (ii) the microcapsule shell thickness (in the case of a core-shell microcapsule) and (iii) the nature of the encapsulating material present in the microcapsule.

With regard to the size, it is known that a population of microcapsules is typically characterized by a distribution of microcapsule sizes. The shape of this size distribution may affect the way the at least one volatile ingredient is released under shear stress. For example, the size distribution may be narrow, with merely all microcapsules being deformed or broken in the same way and under same shear stress conditions, thereby inducing a pronounced boost of release. Conversely, if the size distribution is broad, then the larger microcapsules may be deformed and even broken under a lower shear stress than the smaller ones, or the duration of the shear stress application may need to be longer for smaller microcapsules than for larger ones, thereby inducing a shear stress-dependent or time-dependent release. In some cases, the size distribution may even be bimodal or multimodal, providing more complex release profiles. Varying the applied load, in particular on a tribometer pin probe, and the probe velocity, it is possible to explore such complex release profiles easily.

In an embodiment, the microcapsules are core-shell microcapsules. Core-shell microcapsules are regularly used for fragrance ingredients. Typically, core-shell microcapsules have a polymeric shell surrounding a core comprising the volatile ingredient(s).

The microcapsule shell thickness is typically from about 0.01 to about 5 μm, more particularly from about 0.05 to about 2.5 μm, still more particularly from about 0.1 to about 1.5 μm. However, the present method may also be applied to larger microcapsules with a larger shell thickness.

The microcapsule size is typically from about 0.1 to about 100 μm, more particularly from about 1 to about 50 μm, still more particularly from about 5 to about 30 μm. However, the present method may also be applied to larger microcapsules with a larger size.

Encapsulating materials useful for fragrance encapsulation include, but are not limited to, gelatin and gelatin complexes with arabic gum or carboxymethyl cellulose; polysaccharide complexes, such as alginate complexes with metal ions, especially calcium ions; thermoplastic polymers, such as poly(vinyl alcohol), poly(amides) and the like; inorganic materials, such as silicates and metal oxides; thermosetting resins, such as aminoplast resins, polyurea and polyurethane resins, poly(meth)acrylate resins; and the like. There is principally no limitation as to the nature of the encapsulating materials that can be investigated by the method according to the present invention.

In all cases the method according to the invention provides a universal way to compare the release performance of microcapsules under well-defined shear stress conditions, in particular by setting the applied load p and the velocity of the probe.

The amount of volatile ingredient(s), e.g. perfume ingredients, released from the microcapsules upon application of the kinetic frictional shear stress τ and the time-dependent release profile thereby obtained are the key assessment criteria delivered by the method according to the present invention.

The amount of volatile ingredient(s) released from the microcapsules may be determined by using headspace analytical techniques known in the art. For example, the headspace may be pumped through a cold trap where the volatile ingredient(s) condensate. The trap may then be transferred to a gas chromatographic apparatus where the volatile ingredient(s) are evaporated and subsequently analyzed and quantified. Alternatively, the cold trap may be replaced by an adsorbent and the adsorbed volatile ingredient(s) may be desorbed thermally or by using a suitable solvent before being analyzed chromatographically. A portion of the headspace may also be sampled and directly applied to a chromatographic column.

However, in the context of the present invention, it is preferable to use in-line measurement methods, which allow continuous quantification of the at least one volatile ingredient released during application of the kinetic frictional shear stress τ. Thereby, it is possible to obtain not only the total amount of volatile ingredient(s) released, but also the time-dependent release profile. Continuous, in-line headspace measuring instruments include, but are not limited to, gas analyzers, such as Infra-Red Spectrometers, Flame-Ionization Detectors, Photon-Ionization Detectors, Proton Transfer Reaction Mass Spectrometer (PTR-MS), Analytical Ion Mobility Spectrometer (A-IMS), and the like. Some of these instruments, such as Flame-Ionization Detectors or Photon-Ionization Detectors (PID), measure the total amount of all volatile ingredients released, without providing any information on the composition of the headspace, while other instruments, such as a Proton Transfer Reaction Mass Spectrometer (PTR-MS) or an Analytical Ion Mobility Spectrometer (A-IMS), do also provide information on the composition of the headspace.

Figure 5:
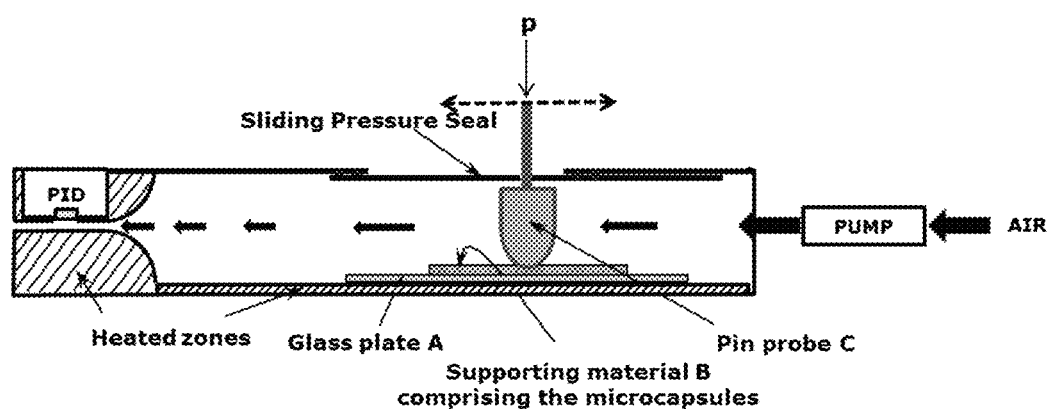

In an embodiment, the microcapsules and the probe and preferably also the supporting material, if present—are located in a chamber and the chamber is connected to a detector, e.g. a PID, via a thermally insulated tubing and a flow of air is pumped through this system. Such an arrangement is shown in FIG. 5. The relevant components depicted in FIG. 1 are therefore enclosed in an essentially cuboid cell through which the air flow is applied. In order to allow the motion of the pin probe, the cell is closed by a rubber sliding pressure seal having a slit in the direction of the motion.

Preferably, the underlying plate and the detector are heated to a temperature of from about 25 to about 120° C., more particularly from about 40° C. to about 90° C., for example 70±10° C. Increasing the temperature of the measurement set-up enhances the transfer of the perfume to the air flow and improves the sensitivity of the detector. In one embodiment, the air flow is from about 100 to about 500 ml/min, more particularly from about 200 to about 400 ml/min, for example 280±50 ml/min.

Optionally, the output of the PID is connected to a glass nose cone for in-line olfactory assessment.

Typical perfume release curves are shown in FIG. 3. The three perfume release curves have been measured with a pin-on-plate tribometer at different load values p of 2 N, 5 N, and 20 N, respectively, and at a constant pin probe velocity u of 10 mm/s.

The release curves (4), (5), and (6) are characterized by an initial plateau where the signal of the detector is almost zero, followed by a steep increase when the released perfume molecules start to enter the detector following the action of the tribometer pin probe. Then, the curves undergo a series of oscillations within about 1 minute, which are due to the pin probe periodically leaving and reentering the area where the supporting material B is located on the glass plate A (see FIG. 1). These oscillations weaken with time and the curves finally reach a nearly constant value for an additional 0.5 minute, at which time the measurement is typically ended by the operator.

Practically, the maximum of each release curve (4), (5), or (6) is taken as a measure of the release performance of the microcapsules, and corresponds to the maximal amount of volatile ingredient(s) released from microcapsules under defined conditions of load p, contact surface area s and probe pin velocity u. The absolute maxima of the three release curves (4), (5), and (6) in FIG. 3 are indicated by the numbers (1), (2) and (3), respectively. The value of each curve at its absolute maximum is a fraction of the maximal releasable amount and is expressed in wt % based on the maximal releasable amount.

The maximal releasable amount is measured as described above in connection with FIG. 4. Under these conditions, all microcapsules are broken, and the signal corresponds, therefore, to the maximum signal achievable for a given measurement set-up.

The maximal releasable amount is given by the area under the maximal release curve. The area under the maximal release curve may obtained by integrating the detector signal or by graphical triangulation.

The latter method is sufficiently accurate for the sake of the present invention, because the maximal releasable amount of volatile ingredient(s) is considerably higher than the peak value values measured when the microcapsules are embedded in or deposited on the supporting material and submitted to a load of not more than 10 N, more particularly 5 N and still more particularly 2 N.

The applicant has found that, in order to generate perfume benefits, as measured by the olfactive performance scores obtained by panellists, the measured maximal amount of perfume released from the microcapsules, upon application of a kinetic frictional shear stress $\tau$ of from $0.5 \times 10^4$ N/m$^2$ to $1 \times 10^4$ N/m$^2$ under a load of 2 N, through a contact surface area of from $5.2 \times 10^{-5}$ m$^2$ to $6 \times 10^{-5}$ m$^2$ and with a shear rate of $11 \pm 0.25$ s$^{-1}$, should be higher than 5 wt %, more preferably higher than 7 wt % of the maximal amount of releasable volatile ingredient from neat microcapsules deposited on a hard surface upon application of load of 20 N, through a contact surface area of 2.8 mm$^2$ and with a velocity of 10 m/s.

Shells of core-shell microcapsules that are particularly suitable for providing the desired release profile disclosed hereinabove include thermosetting resins shells, such as aminoplast shells obtained by polycondensation of amino-aldehyde pre-condensates, polyurea shells obtained by polyaddition of polyamines and poly isocyanates, poly(acrylate)-based shells, and the like, and shells obtained by combining these resins.

The microcapsules may be incorporated into the supporting materials mentioned hereinabove by various means known in the art.

The microcapsules may be provided in the form of a suspension in a water phase, usually called a slurry, comprising typically 35 to 45 wt % microcapsules, based on the total weight of the suspension.

In a preferred embodiment, a slurry comprising the microcapsules is put in contact with a porous supporting material, wherein the slurry can diffuse freely, and the supporting material comprising the microcapsules is then dried, either at room temperature or in a thermostated oven or a hot air dryer. Preferably, the microcapsules are dried overnight at room temperature.

The amount of microcapsules embedded in or deposited on the supporting material is preferably from about 0.001 to about 0.01 kg/m$^2$, more preferably from about 0.002 to about 0.005 kg/m$^2$. The resulting material may then be disposed on the glass plate of the tribometer and the measurement is carried out as described hereinabove.

In an embodiment, the supporting material comprising the microcapsules is prepared by mixing the slurry with a gel-forming material. For example, the gel-forming material may be dissolved in the slurry and gelation initiated by means known in the art. Suitable gel-forming materials include gel-forming polymers, such as gellan gum, alginate, gelatin, polyacrylate cross-polymers, and the like, and gel-forming monomers, such as acrylamide and bis-acrylamide. The resulting gel can then be disposed on the glass plate of the tribometer and the measurement is carried out as described hereinabove In another embodiment, the supporting material comprising the microcapsules is prepared by mixing the slurry with various fillers, such as microcrystalline cellulose, clays, minerals, and the like, in order to thicken said slurry to obtain a self-holding paste. The resulting paste may then be disposed on the glass plate of the tribometer and the measurement is carried out as described hereinabove.

In an embodiment, the slurry is spray-dried in a conventional spray-drying tower, e.g. using a two-fluid nozzle, or spin dried in a conventional spin dryer. If desired, at least one hydrocolloid may be added to the microcapsule slurry, as such or in the form of an aqueous solution. Typical hydrocolloids include starch, modified starch, such as dextrin-modified with octenyl succinate anhydride, and arabic gum. Optionally, maltodextrins and sugar alcohols, such as sorbitol, mannitol or maltitol may also be added. The resulting powder may then be deposited on the glass plate of the tribometer and the measurement is carried out as described herein above.

EXAMPLES

The present invention is further exemplified by means of the following non-limiting examples:

Example 1: Determination of the Kinetic Friction Force

The kinetic friction force effectively applied by the pin probe in a pin-on-plate tribometer having a cell as shown in FIG. 5 is determined by two key contributions:
(i) the kinetic friction force effectively produced by the friction between the pin probe C and the supporting material B as shown in FIG. 1, and
(ii) the instrument kinetic friction force exerted by the cell top rubber sliding pressure seal on the stem of the pin probe.

Contribution (i) was measured at a pin probe velocity of 10 mm/s after having removed the rubber closing and found to vary between 0.2 and 2.2 N upon increasing the load from 0.7 to 10 N for a blotting paper having a thickness of 1 mm (Table 1).

TABLE 1

Kinetic friction force as function of load for blotting paper

| Loading force [N] | Kinetic friction force [N] | Standard deviation [N] | Kinetic frictional coefficient |
|---|---|---|---|
| 0.73 | 0.23 | 0.01 | 0.32 |
| 2.65 | 0.55 | 0.07 | 0.21 |
| 3.58 | 0.71 | 0.05 | 0.20 |
| 4.54 | 0.96 | 0.04 | 0.21 |
| 5.43 | 1.18 | 0.07 | 0.22 |
| 10.04 | 2.19 | 0.14 | 0.22 |

The kinetic friction force depends furthermore on the velocity of the probe. As shown in Tables 2, the contribution (i) to the kinetic friction force under a load of 2 N varies from 0.45 to 0.6 N when the probe velocity increases from 5 to 50 mm/s for blotting paper.

TABLE 2

Friction force as function of pin-probe velocity for blotting paper

| Pin probe velocity [mm/s] | Kinetic friction force [N] | Standard deviation [N] |
|---|---|---|
| 5 | 0.46 | 0.19 |
| 10 | 0.53 | 0.18 |
| 20 | 0.54 | 0.18 |
| 30 | 0.57 | 0.18 |
| 40 | 0.62 | 0.18 |
| 50 | 0.60 | 0.18 |

Knowing the contact surface area of the pin robe and the supporting material comprising the microcapsules, the above results allow for the calculation of the kinetic frictional shear stress as function of load or pin probe velocity.

The contact surface area may be determined by inking the pin probe with a viscous dye and measuring the colored surface area produced when contacting the probe with the surface under a given load (dye method). Alternatively, a pressure pad may be used, in which case the portion of the pressure sensor array of the pad, which is deformed under pressure, is calculated digitally. Table 3 shows the contact surface areas for different loads, as measured using the dye method mentioned above.

TABLE 3

Contact surface as a function of the load applied to the pin probe

| Load [N] | Surface area on deformable blotting paper [mm2] | Surface area on glass surface [mm2] |
|---|---|---|
| 0 | 2.8 ± 0.5 | |
| 1 | 28 ± 5 | |
| 2 | 56 ± 4 | |
| 5 | 84 ± 2 | |
| 10 | 98 ± 2 | |
| 20 | 112 ± 1 | 2.8 ± 0.5 |

The values of the kinetic frictional shear stress applied to the microcapsules are given in Table 4 at different loads with a constant probe velocity of 10 mm/s.

TABLE 4

Kinetic frictional shear stress as a function of the load for blotting paper

| Load [N] | Surface area min [mm$^2$] | Surface area max [mm$^2$] | Kinetic friction force min [N] | Kinetic friction force max [N] | Kinetic frictional stress min [N/m$^2$] | Kinetic frictional stress max [N/m$^2$] |
|---|---|---|---|---|---|---|
| 1 | 23 | 33 | 0.15 | 0.25 | (0.55 ± 0.1)*10$^4$ | (1.35 ± 0.2)*10$^4$ |
| 2 | 52 | 60 | 0.3 | 0.5 | (0.54 ± 0.04)*10$^4$ | (0.9 ± 0.06) * 10$^4$ |
| 5 | 82 | 86 | 0.8 | 1.4 | (0.95 ± 0.03)*10$^4$ | (1.3 ± 0.03)*10$^4$ |
| 10 | 96 | 100 | 1.8 | 2.4 | (2.08 ± 0.03)*10$^4$ | (2.5 ± 0.03)*10$^4$ |

The conditions for measuring the release performance of microcapsules were chosen as follows:

| | |
|---|---|
| Deformable material: | blotting paper |
| Load: | 2N |
| Contact surface area: | 56 ± 4 mm$^2$ |
| Shear rate: | 11 ± 0.25 s$^{-1}$ |
| Probe velocity: | 10 mm/s. |

The corresponding kinetic frictional shears stress τ applied to the microcapsules in blotting paper was from about 0.5×10$^4$ to about 0.96×10$^4$ N/m$^2$ on blotting paper.

Example 2: Determination of the Perfume Release Rate Under Friction and Comparison with Results from Indentation Measurements and Olfactive Assessment Scores A perfume composition comprising the perfume ingredients listed in Table 5 was encapsulated in various core-shell microcapsules as described in Table 6.

TABLE 5

Perfume composition

| Perfume Ingredient | Weight % |
|---|---|
| 3-methylbut-2-en-1-yl acetate | 4 |
| hexyl acetate | 6 |
| (E)-3,7-dimethylocta-2,6-dienal | 3 |
| 2-(tert-butyl)cyclohexyl acetate | 15 |
| 3,7-dimethylocta-1,6-dien-3-ol | 8 |
| (3aR,6S,7aS)-3a,4,5,6,7,7a-hexahydro-1H-4,7-methanoinden-6-yl acetate | 30 |
| 1-methyl-4-prop-1-en-2-ylcyclohexene | 4 |
| (E)-4-(2,6,6-trimethylcyclohex-1-en-1-yl)but-3-en-2-one | 10 |
| 5-heptyloxolan-2-one | 10 |
| 2-(2-(4-methylcyclohex-3-en-1-yl)propyl)cyclopentanone | 10 |

TABLE 6

Types of core-shell microcapsules used

| | |
|---|---|
| Sample #1 | Double layer aminoplast microcapsule obtained by the method disclosed in WO 2017/001672 A1. Microcapsule size: 18 μm |
| Sample #2 | Anionic aminoplast terpolymer microcapsules obtained according to the method disclosed in U.S. Pat. No. 8,119,587 B2, Example 1.3, Process P5.1. Microcapsule size: 20 μm |
| Sample #3 | Polyurea microcapsules obtained according to the method disclosed in US 2013/0089590 A1, Example 1. Microcapsule size: 10 μm |
| Sample #4 | Same as Sample 2, but having a size of 7 μm |
| Sample #5 | Cationic aminoplast microcapsules obtained according to the method disclosed in WO 2017/001672 A1. Microcapsule size: 10 μm |

The microcapsules were used in the form of suspensions in a water phase, usually called slurries, comprising typically 35 to 45 wt % microcapsules, based on the total weight of the suspension. These suspensions were diluted 5000 times with deionized water and 100 μl of each of these diluted suspensions was deposited on a blotting paper having a density of 175±10 g/m$^2$, a water absorption capacity of 500 ml/m$^2$, and dimensions of 75 mm×28 mm. After complete absorption had occurred, the blotting paper was dried overnight at room temperature to obtain the sample. The thickness of the blotting paper under a pressure of 2 N/(56±4) mm$^2$ (=about (3.6±0.3) 10$^4$ N/m$^2$) was about 0.92±0.02 mm.

The sample was then placed in the measuring cell on a glass plate and the air flow was switched on. The sample and detector temperature was set to 70±2.° C., as measured with thermocouples.

The measurement was started by applying the loaded pin probe to the sample and allowing the pin probe to move back and forth so that the velocity of the moving pin probe in contact with the sample was 10 mm/s in each direction. Taking the thickness of the blotting paper under pressure of 0.92±0.02 mm, as mentioned herein above, the corresponding shear rate was 11±0.25 s$^{-1}$.

A photon ionization detector (PID) was used for detection of the perfume release. The signal of the PID was monitored as a function of time and recorded. The value at the maximum of the signal was taken as peak value, i.e. maximal amount of perfume released under the experimental conditions described hereinabove. The air flow rate in the cell and in the detector was 280 ml/min.

The total releasable amount of perfume was determined repeating the measurements under the following modified conditions:

i. the blotting paper was removed and an amount of slurry was directly deposited on the glass plate, wherein this amount was ¹/₁₀ of the amount of slurry applied on the blotting paper, as mentioned hereinabove; and ii. the load was increased to 20 N.

The total releasable amount of perfume was determined by using the maximum of the signal.

The indentation measurements were performed according to the method described in Z. Zhang; G. Sun; "Mechanical Properties of Melamine-Formaldehyde microcapsules," J. Microencapsulation 18 (2001) 593-602.

The olfactive assessment was performed by a panel of 10 panellists by gently rubbing terry towelling fabrics that had been rinsed with 21 g liquid fabric care conditioner containing 0.5 wt % microcapsules in a side-loaded washing machine (20 L capacity, loaded with 1 kg terry towelling, washed beforehand with an unperfumed laundry detergent); a rinse cycle was performed at a temperature of 20° C., followed by spin drying.

The post-rub olfactive evaluation was performed after line drying the terry towelling for 24 hours at room temperature. This evaluation was performed by gently rubbing one part of the terry towelling on another part of same terry towelling. A binary performance score was given: POOR for samples providing a barely to moderately perceivable fragrance impact, and GOOD for samples providing a strongly to very strongly perceivable fragrance impact.

TABLE 7

Peak values for microcapsules submitted to a kinetic frictional shear stress of $0.73 \pm 0.23 \times 10^4$ $N/m^2$ and comparison to results of indentation measurements and total releasable perfume amount and

| Sample | Maximal release from neat microcapsules [arbitrary unit] | Maximal release of sample [wt %] | Nominal rupture stress (from indentation measurements) [MPa] | Olfactive assessment |
|---|---|---|---|---|
| #1 | 532.3 | 8.9 | 10.6 | GOOD |
| #2 | 530.0 | 7.9 | 4.4 | GOOD |
| #3 | 464.0 | 2.2 | 4.2 | POOR |
| #4 | 448.7 | 4.3 | 1.7 | POOR |
| #5 | 419.3 | 6.2 | 2 | GOOD |

As apparent from Table 7, the method according to the present invention provides release peak values that are in line with the olfactive assessment score, which is not the case of the nominal rupture stress measured by applying indentation measurements.

Furthermore, the method according to the present invention is sensitive to the nature of the microcapsules and can be used to develop microcapsules having the desired perfume release performance. In Table 7, the microcapsules having the best release performance are based on aminoplast chemistry and are not too small. Polyurea microcapsules and small aminoplast terpolymer microcapsules are less performing.

The invention claimed is:

1. A method of assessing the release performance of microcapsules comprising at least one volatile ingredient, the method comprising the steps of:
   a. applying a plurality of said microcapsules to an underlying surface;
   b. applying a kinetic frictional shear stress τ through a contact surface of a probe under a predefined load p, a predefined contact surface area and a predefined shear rate to said plurality of microcapsules;
   wherein:
      the contact surface area is defined as the area of the contact surface of the probe through which the predefined load is applied; and
      the shear rate is defined as the velocity u of said probe relative to the underlying surface in a direction parallel to said underlying surface divided by the distance between the probe and the underlying surface; and,
   c. measuring the amount of the at least one volatile ingredient released per second from said microcapsules under said kinetic frictional shear stress τ.

2. The method of claim 1, wherein:
   the microcapsules are core-shell microcapsules or particles in which the at least one volatile ingredient is distributed in the form of a plurality of inclusions and/or droplets.

3. The method of claim 1, wherein the at least one volatile ingredient is a flavour or a fragrance ingredient.

4. The method of claim 1, wherein the microcapsules are embedded in and/or are deposited on a supporting material, said supporting material selected from: an adhesive, a granulated material, a powder, a woven material, a non-woven material, a gel, an emulsion, a cream, a polymer, or a combination thereof.

5. The method of claim 4, wherein the supporting material comprises a liquid.

6. The method of claim 1, wherein the kinetic frictional shear stress τ is applied by a tribometer.

7. A method of assessing the release performance of microcapsules comprising at least one volatile ingredient, the method comprising the step of:
   utilizing a tribometer.

8. A composition comprising a plurality of microcapsules in a suspending medium, wherein said microcapsules comprise at least one volatile ingredient, and wherein more than 5 wt % of said at least one volatile ingredient is released upon application of a kinetic frictional shear stress τ of from $0.5 \times 10^4$ $N/m^2$ to $1 \times 10^4$ $N/m^2$ under a load of 2 N, through a contact surface area of from $5.2 \times 10-5$ $m^2$ to $6 \times 10-5$ $m^2$ and with a shear rate of $11 \pm 0.25$ s–1, wherein
   the contact surface area is defined as the area of the contact surface of a probe through which the predefined load is applied; and
   the shear rate is defined as the velocity of said probe relative to an underlying surface in a direction parallel to said underlying surface divided by the distance between the probe and the underlying surface; and
   the weight percentage of the one or more volatile ingredient released refers to the maximal amount of releasable volatile ingredient from neat microcapsules deposited on a hard surface upon application of load of 20 N, through a contact surface area of 2.8 $mm^2$ and with velocity of 10 m/s.

9. The method of claim 2, wherein the at least one volatile ingredient is a flavour or a fragrance ingredient.

10. The method of claim 2, wherein the microcapsules are embedded in and/or are deposited on a supporting material, said supporting material selected from: an adhesive, a granulated material, a powder, a woven material, a non-woven material, a gel, an emulsion, a cream, a polymer, or a combination thereof.

11. The method of claim 10, wherein the supporting material comprises a liquid.

12. The method of claim 6, wherein the tribometer is a pin-on-plate tribometer.

13. The method of claim 7, wherein the tribometer is a pin-on-plate tribometer.

* * * * *